(12) United States Patent
Dailey

(10) Patent No.: US 6,547,714 B1
(45) Date of Patent: Apr. 15, 2003

(54) MAGNETIZED SCLERAL BUCKLE FOR USE WITH SILICONE MAGNETIC FLUIDS IN THE TREATMENT OF RETINAL DISEASES

(76) Inventor: James P. Dailey, 222 Superior Ave., Erie, PA (US) 16505

( * ) Notice: Subject to any disclaimer, the term of this patent is extended or adjusted under 35 U.S.C. 154(b) by 213 days.

(21) Appl. No.: 09/654,636

(22) Filed: Sep. 5, 2000

Related U.S. Application Data

(62) Division of application No. 09/075,698, filed on May 11, 1998, now Pat. No. 6,135,118.
(60) Provisional application No. 60/046,171, filed on May 12, 1997.

(51) Int. Cl.[7] .................................................. A61N 1/00
(52) U.S. Cl. .......................................... 600/12; 600/15
(58) Field of Search ........................................ 600/9–15

(56) References Cited

U.S. PATENT DOCUMENTS

| | | | | |
|---|---|---|---|---|
| 3,626,940 A | * | 12/1971 | Zaffaroni | 600/15 |
| 4,902,292 A | * | 2/1990 | Joseph | 604/294 |
| 5,181,922 A | * | 1/1993 | Blumenkanz et al. | 128/898 |
| 5,389,981 A | * | 2/1995 | Riach, Jr. | 351/158 |
| 5,722,952 A | * | 3/1998 | Schachar | 604/290 |
| 6,007,578 A | * | 12/1999 | Schachar | 623/11.11 |
| 6,117,170 A | * | 9/2000 | Batdorf, Sr. | 602/41 |
| 6,197,056 B1 | * | 3/2001 | Schachar | 623/4.1 |

* cited by examiner

Primary Examiner—Samuel G. Gilbert
(74) Attorney, Agent, or Firm—Whitham, Curtis & Christofferson, P.C.

(57) ABSTRACT

The basic principle in repairing retinal detachments is closing the retinal break. An internal tamponade is a material suitable for intraocular use which is used to directly close a retinal break. A scleral buckle is a flexible device which can conform to and allow movement of the sclera. A new method to treat retinal detachment is to combine usage of a magnetic fluid tamponade with a magnetized flexible scleral buckle, which effects tamponade of the retina without interfering with vision. A substantial percentage of complicated retinal detachments currently go on to blindness despite multiple attempts at surgical intervention because of our inability to tamponade retinal breaks in certain locations. In a cross-sectional view of the eye, the retina and choroids sit on the sclera. Each break in the retina therefore sits on a specific location on the sclera. The magnetic scleral buckle (msb) is positioned on the exterior aspect of the sclera at the location of the retinal break, employing the msb's trans-scleral magnetic field, and magnetically attracts the silicone magnetic fluid to the retinal break. This system of silicone magnetic fluid and magnetized scleral buckle can thus tamponade retinal breaks wherever they occur.

4 Claims, 2 Drawing Sheets

MAGNETIZED SCLERAL BUCKLE FOR USE WITH SILICONE MAGNETIC FLUIDS IN THE TREATMENT OF RETINAL DISEASES

CROSS REFERENCE TO RELATED APPLICATIONS

This application is a division of Ser. No. 09/075,698 filed May 11, 1998 now U.S. Pat. No. 6,135,118 which is based on U.S. Provisional Application Ser. No. 60/046,171, filed May 12, 1997, incorporated herein by reference in full.

FIELD OF THE INVENTION

This invention relates to methods for treating disorders using a magnetic fluid. More specifically, the invention relates to a method for treating a detached retina using a magnetic fluid in combination with a magnetized scleral buckle, and to methods for directing delivery of a compound by using a magnetic fluid carrier.

BACKGROUND OF THE INVENTION

The mammalian eye comprises two chambers. The anterior chamber is bounded by the cornea and lens, and contains the aqueous humor. The volume behind the lens contains the vitreous humor, with the retina attached to the back wall of the eye. The retinal layer is not firmly attached to the eye, and can become detached, resulting in eventual death of the retina and loss of vision. The retina may detach along an edge, e.g. as the result of traumna, or as the result of a tear allowing fluid to leak underneath the retina and separate the retina from the underlying choroid. Retinal detachment can be treated by means of a scleral buckle, a silicone band that encircles the eye and compresses the wall of the eye inward against the retina. Alternatively, the vitreous humor may be replaced in whole or in part with a tamponade, a heavy liquid or gas intended to flatten the retina against the choroid.

Currently used internal tamponades ($SF_6$, $C_3F_8$, silicone oil) float up, leaving the inferior retina unprotected, or sink down (fluorosilicone), leaving the superior retina unprotected. Current tamponades also fill the vitreous cavity, decreasing vision, and contact anterior chamber structures, causing cataract and glaucoma.

SUMMARY OF THE INVENTION

A new method for treating retinal detachment is provided, combining use of a magnetic fluid tamponade with a magnetized scleral buckle, which effects tamponade of the retinal margin without interfering with vision.

One aspect of the invention is a method for treating retinal detachment, by administering to the vitreal chamber a sufficient amount of a magnetic fluid, and applying a magnetized scleral buckle to the eye.

Another aspect of the invention is a magnetic fluid tamponade suitable for use in the eye.

Another aspect of the invention is a magnetized scleral buckle suitable for use in the method of the invention.

Another aspect of the invention is a method for delivering a compound to a relatively inaccessible location, by combining the compound with a magnetic fluid, administering the resulting composition at an accessible location, and directing the composition to the relatively inaccessible location by magnetic attraction.

One object of the invention is to provide a method and apparatus for effecting a retinal tamponade along the periphery of the retina, without contacting the lens or anterior chamber structures, or obstructing the vitreous cavity.

Another object of the invention is to provide a means for shielding the macula from radiation retinopathy.

Another object of the invention is to provide for local delivery of intraocular chemotherapeutic or radiotherapeutic agents.

Another object of the invention is to provide a stable magnetic silicone fluid.

Another object of the invention is to provide a magnetized scleral buckle.

DETAILED DESCRIPTION

Definitions

Figure 1:
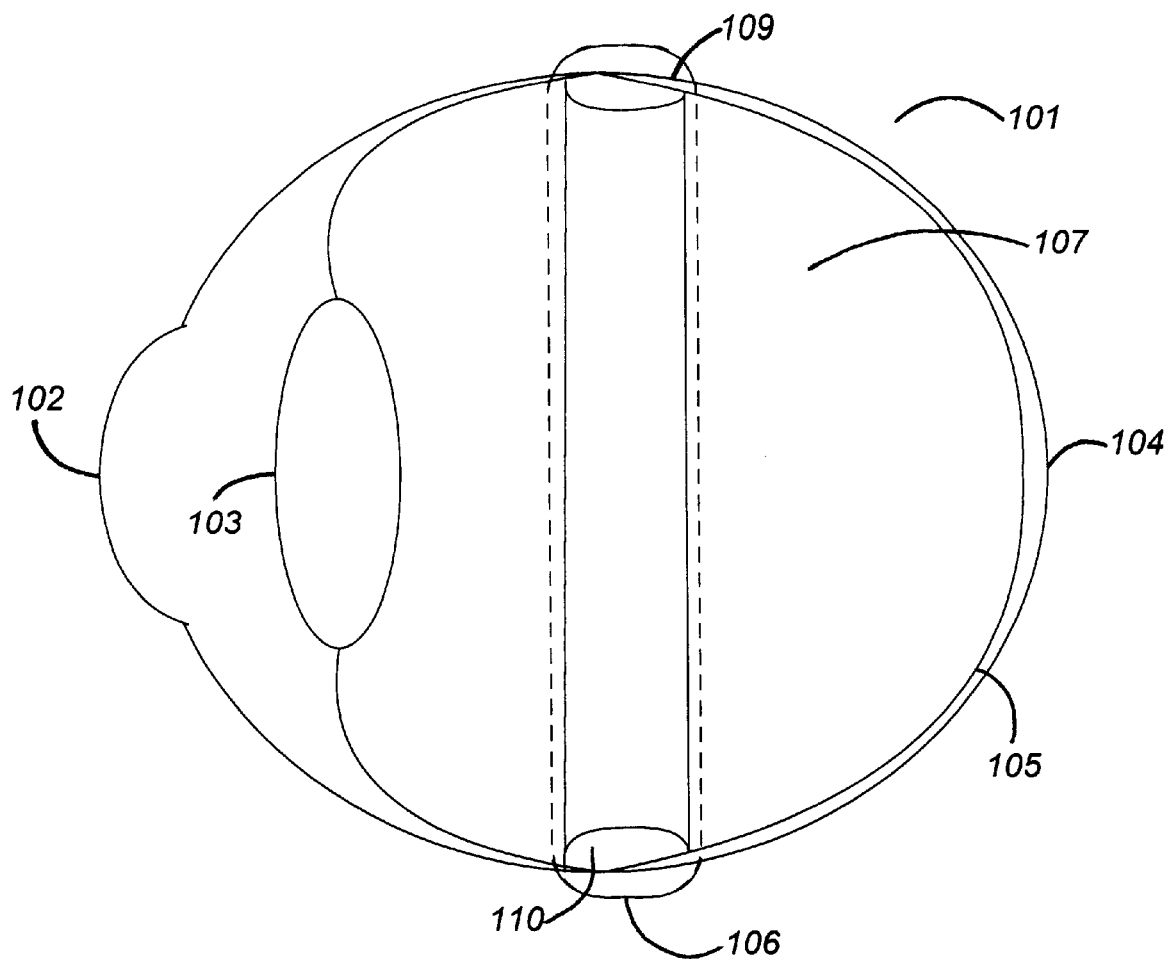
FIG. 1 is a cross-sectional view of an eye having a magnetized scleral buckle and a magnetic fluid tamponade.

The term "magnetic fluid" as used herein refers to a biocompatible liquid having magnetic particles dispersed throughout. Magnetic fluids can be manipulated using magnetic fields.

The term "biocompatible" refers to materials which do not cause undue inflammation or injury when in extended contact with living tissue.

The term "effective amount" as used herein refers to an amount of magnetic fluid sufficient to hold a detached retina in place. In general, an effective amount will be the amount necessary to form a ring around the inside of the vitreal chamber having a thickness of at least about 1 mm, and a width of about 1 to about 7 mm.

The term "cross-linkable polymer" refers to a flexible plastic polymer which can be rendered rigid by addition of a crosslinking agent or catalyst.

The term "magnetic particles" refers to metallic particles that are attracted to magnetic fields.

The term "relatively inaccessible location" refers to a site within the body that is difficult to directly access through standard surgical techniques without undue or unacceptable damage to surround tissue. Examples of relatively inaccessible locations include intracranial regions and intraocular sites, where surgical access can carry the risk of brain damage or loss of vision.

The term "exoplant" or "localized scleral exoplant" refers to a generally flat patch that is sutured or adhered to the outer surface of the eye.

General Method

Magnetic fluids useful in the invention are preferably biocompatible. Thus, the magnetic fluid preferably comprises a non-toxic polymer carrier, such as a fluid dimethylsiloxane, hydrogel or the like. The fluid may further comprise surfactants and/or dispersing agents to stabilize the combination of polymer and magnetic particles. A presently preferred stabilizer is a block polymer having a central block of poly(3-cyanopropyl)methylsiloxane flanked by blocks of polydimethylsiloxane. Block copolymers are often more efficient than homopolymers as dispersion stabilizers. The stabilizer comprises "anchor" blocks which strongly absorb onto the magnetic particle surface, and "tail" blocks which protrude into the medium. Triblock copolymers are preferred having a poly(3-cyanopropyl)methylsiloxane (PCPMS) "anchor" block flanked by two polydimethylsiloxane (PDMS) "tail" blocks. Approximately equal volumes of stabilizer and magnetic particles are used, and typically together constitute about 2% to about 50% of the volume of the magnetic fluid, preferably about 5% to about 30%, most preferably about 10% by volume. The ratio of stabilizer to magnetic particles is from about 1:10 to about 10:1, preferably from about 3:5 to about 5:3, most preferably about 1:1 by volume. The remainder of the magnetic fluid comprises the non-toxic biocompatible carrier, and optionally other stabilizers and preservatives.

The block copolymer stabilizers are made according to the method described in Li et al., "Polydimethylsiloxane-b-Poly(3-cyanopropyl) methylsiloxane-b-Polydimethylsiloxane Triblock Suspension Stabilizers", Polymer Preprints, August, 1996, which is incorporated by reference herein in its entirety.

The magnetic particles are any ferromagnetic element or compound, including without limitation Fe, Ni, Co, $Fe_2O_3$, Neodymium, Samarium, and the like, and are preferably about 2–10 nm in maximum diameter. The medium is a polyalkylsiloxane, such as polydimethylsiloxane.

The amount of stabilizer used will depend upon the concentration of magnetic particles required to hold the tamponade in place with a magnetized scleral buckle of given magnetic strength. This may be determined empirically by those of ordinary skill.

The stabilizer, comprising an anchor block which binds to metal and two tail blocks which are compatible with silicone fluid, is used to suspend magnetic particles in silicone fluid. The anchor blocks of poly(3-cyanopropyl)methylsiloxane (PCPMS) with reactive cyano end groups are prepared using an anionic redistribution reaction of cyclic monomers. Li et al., supra. The stabilizer having a PCPMS anchor block flanked by two polydimethylsiloxane (PDMS) tail blocks are formed using lithium silanolate terminated PCPMS to polymerize hexamethyltrisiloxane. Li et al., supra Formation of Anchor Blocks

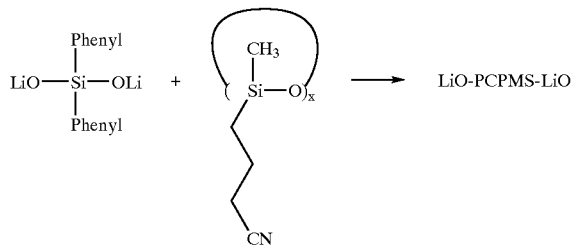

Formation of Dispersion Stabilizer

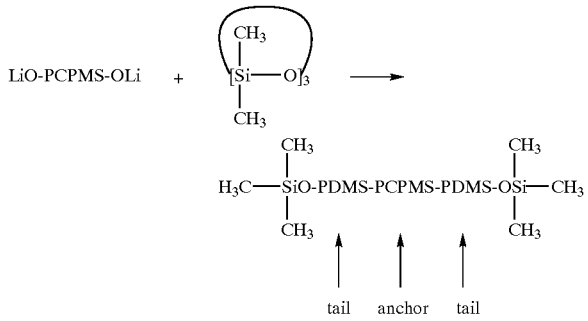

$\gamma$-$Fe_2O_3$ powder (or other magnetic particles) is dispersed in silicone monomer containing minor amounts of the triblock stabilizers with ultrasonification.

While not being bound to a theory, it is believed that the stabilizer produces a stable colloidal suspension because:
1. The block copolymers are strongly absorbed onto the metal surface via the central cyano-containing PCPMS "anchor" block.
2. The "tail" blocks of PDMS extend into the PDMS medium. In close proximity, the mutual repulsion of these tails causes them to extend as far as possible into the medium.
3. The particles tend not to coagulate because approach of the particle—stabilizer complexes causes an unfavored decrease in entropy.
4. Also, coagulation of the particles requires desorption or lateral surface movement of the stabilizers which is an unfavored energy requirement.

The scleral buckle comprises a flexible biocompatible material, suitable for application to the sclera. The buckle is preferably a flexible silicone band, dimensioned to fit snugly around the eye and gently compress the eye so that the inner surface of the vitreal chamber is urged into contact with the periphery of the retina. The buckle is preferably fabricated by combining medical grade siloxane with magnetic particles (as described above for the magnetic fluid) prior to cross-linking or curing. Buckles can be provided in the form of strips or rings, generally as a relatively flat band. Rings are provided in a plurality of different diameters, to accommodate eyes of different sizes. Strips can be provided in any length, and cut to fit at the time of application, followed by connecting the ends of the strip. Strips and rings are preferably cast in their final form. Scleral exoplants or patches are formed in the same way, and can optionally be provided with positioning straps.

FIG. 1 is a cross-sectional view of an eye 101 having cornea 102, lens 103, choroid 104, retina 105, vitreal chamber 107, magnetic scleral buckle 106 and magnetic fluid 110 of the invention. In the practice of the invention, a subject is generally first diagnosed as having retinal detachment. The method of the invention is particularly suited for treating holes along the periphery of the retina 109. The eye is first subjected to a partial or total vitrectomy (removal of part or all of the vitreous humor) by surgical methods. The magnetic fluid is applied, for example using a syringe, and the magnetic scleral buckle 106 is positioned immobilized in place, generally by suture or adhesive. The scleral buckle attracts the magnetic fluid 110 to an annular position inside the eye, closest to the retinal periphery 109.

Figure 2:
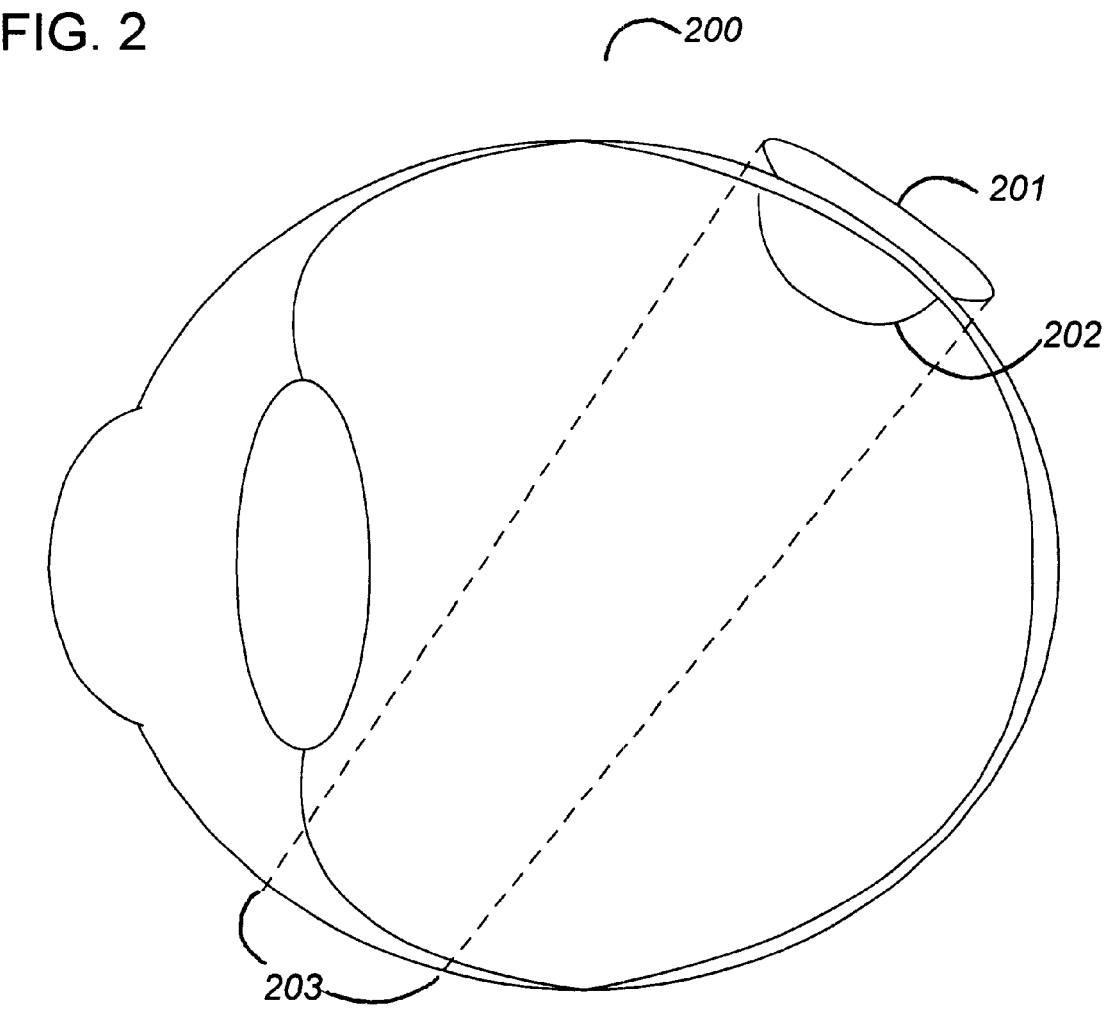
FIG. 2 is a cross-sectional view of an eye having a magnetized exoplant and magnetic fluid.

Detachments in other regions of the retina can also be treated, by positioning the scleral buckle over the detached region, or by applying a magnetized exoplant. FIG. 2 is a cross-sectional view of an eye 200 having a magnetic fluid tamponade 202 held in place by a magnetized exoplant 201. The exoplant 201 can be fixed in place using adhesive, sutures, and/or positioning bands 203. The localized exoplant is also suitable for treating intraocular tumors, when used in combination with a magnetic fluid 202 containing a chemotherapeutic or radiotherapeutic agent. Further, one can employ an exoplant to shield the macula from radiation damage during cancer treatment by applying an exoplant to the sclera such that magnetic fluid injected into the vitreous chamber covers the macula. The magnetic fluid partially shields the macula from the effects of radiation, which may otherwise lead to radiation retinopathy. The exoplant and fluid can be removed at the conclusion of treatment.

An encircling magnetized scleral buckle and magnetic fluid produces a 360 degree ring of magnetic fluid in apposition to the retinal periphery. Furthermore, the central vitreous cavity is free of magnetic fluid, and there is no contact between the magnetic fluid and the lens, anterior chamber structures, and macula.

EXAMPLE

Neodymium/iron particles are dispersed in polysiloxanes with acetoxy functional groups which condense in the presence of atmospheric moisture at low temperature to yield crosslinked polydimethylsiloxane elastomers. These are molded in an appropriate configuration for scleral buckling elements, having about 10% by volume magnetic particles.

What is claimed is:

1. A scleral buckle for treating a detached retina in an eye comprising:

a flexible biocompatible band dimensioned to fit around said eye;

wherein said buckle comprises magnetic particles.

2. The buckle of claim 1, wherein said magnetic particles have a diameter of about 2 to about 10 nm.

3. The buckle of claim 2, wherein said particles comprise iron, nickel, or neodynium.

4. The buckle of claim 1, wherein said buckle exerts pressure sufficient to slightly deform the eye when applied.

* * * * *